(12) United States Patent
Coke et al.

(10) Patent No.: US 11,114,206 B2
(45) Date of Patent: Sep. 7, 2021

(54) VITAL SIGNS WITH NON-CONTACT ACTIVITY SENSING NETWORK FOR ELDERLY CARE

(71) Applicant: Tellus You Care, Inc., San Francisco, CA (US)

(72) Inventors: Tania Abedian Coke, San Francisco, CA (US); Kevin Hsu, San Francisco, CA (US)

(73) Assignee: Tellus You Care, Inc., San Francisco, CA (US)

(*) Notice: Subject to any disclaimer, the term of this patent is extended or adjusted under 35 U.S.C. 154(b) by 610 days.

(21) Appl. No.: 16/149,422

(22) Filed: Oct. 2, 2018

(65) Prior Publication Data

US 2019/0108913 A1 Apr. 11, 2019

Related U.S. Application Data

(63) Continuation-in-part of application No. 16/148,418, filed on Oct. 1, 2018, now Pat. No. 10,410,498.
(Continued)

(51) Int. Cl.
*G16H 50/20* (2018.01)
*G06N 3/08* (2006.01)
(Continued)

(52) U.S. Cl.
CPC ............. *G16H 50/20* (2018.01); *A61B 5/002* (2013.01); *A61B 5/0205* (2013.01);
(Continued)

(58) Field of Classification Search
CPC ........ G16H 50/20; G16H 50/00; G16H 10/60;
A61B 5/0205; A61B 5/0507; A61B 5/002; A61B 5/746; A61B 5/117; A61B 5/6889; A61B 5/1113; A61B 5/6891; A61B 5/747; A61B 5/4076; A61B 5/08; A61B 2503/08; G01S 7/415; G01S 13/88; G01S 7/295;
(Continued)

(56) References Cited

U.S. PATENT DOCUMENTS 9,538,158 B1 1/2017 Rush et al.
9,767,557 B1 9/2017 Gulsun et al.
(Continued)

*Primary Examiner* — Emily C Terrell
(74) *Attorney, Agent, or Firm* — Muirhead and Saturnelli, LLC

(57) ABSTRACT

Determining a physical state of a person includes detecting positions of different portions of the person, transforming detected positions into a point cloud having a density that varies according to movement of each of the portions, correlating movement and position data from the point cloud with known physical state positions and transitions between different states, choosing a particular physical state by matching the data from the point cloud with the particular physical state, and obtaining vital signs of the person during an optimal period of time for automatic capturing of vital signs by detecting when the person is in a particular state. The particular state may be a static state. The static state may be standing, sitting, or laying down. The vital signs may include measuring a breathing rate and measuring a heartbeat rate. Vital signs may be obtained by detecting pulsations in the point cloud representing breathing and heartbeats.

23 Claims, 9 Drawing Sheets

Related U.S. Application Data

(60) Provisional application No. 62/569,405, filed on Oct. 6, 2017.

(51) Int. Cl.
| | |
|---|---|
| *G01S 13/88* | (2006.01) |
| *G06N 3/04* | (2006.01) |
| *G01S 7/295* | (2006.01) |
| *A61B 5/0205* | (2006.01) |
| *A61B 5/0507* | (2021.01) |
| *A61B 5/00* | (2006.01) |
| *A61B 5/117* | (2016.01) |
| *A61B 5/11* | (2006.01) |
| *G01S 7/41* | (2006.01) |
| *G01S 13/02* | (2006.01) |
| *G01S 13/87* | (2006.01) |
| *G01S 13/32* | (2006.01) |
| *A61B 5/08* | (2006.01) |
| *G16H 50/00* | (2018.01) |

(52) U.S. Cl.
CPC ............ *A61B 5/0507* (2013.01); *A61B 5/117* (2013.01); *A61B 5/1113* (2013.01); *A61B 5/6889* (2013.01); *A61B 5/6891* (2013.01); *A61B 5/746* (2013.01); *A61B 5/747* (2013.01); *G01S 7/295* (2013.01); *G01S 7/415* (2013.01); *G01S 13/88* (2013.01); *G06N 3/0445* (2013.01); *G06N 3/08* (2013.01); *A61B 5/08* (2013.01); *A61B 5/4076* (2013.01); *A61B 2503/08* (2013.01); *G01S 13/0209* (2013.01); *G01S 13/32* (2013.01); *G01S 13/878* (2013.01); *G16H 50/00* (2018.01)

(58) Field of Classification Search
CPC .... G01S 13/878; G01S 13/32; G01S 13/0209; G06N 3/08; G06N 3/0445
USPC .......................................................... 701/19
See application file for complete search history.

(56) References Cited

U.S. PATENT DOCUMENTS

| | | |
|---|---|---|
| 2013/0053653 A1 | 2/2013 | Cuddihy et al. |
| 2014/0095181 A1 | 4/2014 | Johnson et al. |
| 2015/0094545 A1 | 4/2015 | Russell et al. |
| 2021/0197834 A1* | 7/2021 | Shaker ................... G01S 7/292 |

* cited by examiner

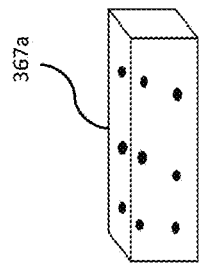
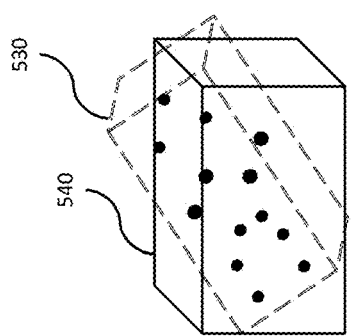
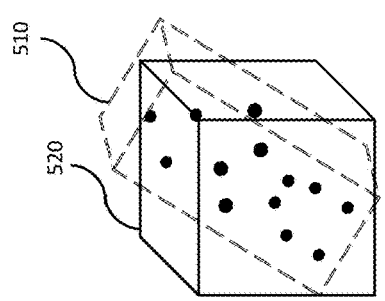
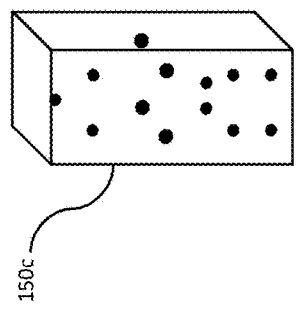
FIG. 5

VITAL SIGNS WITH NON-CONTACT ACTIVITY SENSING NETWORK FOR ELDERLY CARE

CROSS-REFERENCE TO RELATED APPLICATIONS

This application claims priority to U.S. Prov. App. No. 62/569,405, filed on Oct. 6, 2017, and entitled "METHOD AND SYSTEM FOR A NON-CONTACT ACTIVITY SENSING NETWORK FOR ELDERLY CARE", which is incorporated herein by reference.

TECHNICAL FIELD

This application is directed to the field of remote monitoring of activities using interconnected hardware, software, and cloud components, and more particularly to remote monitoring of activities of daily living of elderly people using an ultra-wideband radar and a geometric and AI model trained on appropriate samples.

BACKGROUND OF THE INVENTION

Quick aging of world's population presents an ever growing list and magnitude of challenges to our civilization, ranging from dramatic changes in the modern workforce size and composition, in economy and health insurance, to transformations in family lifestyles and in elderly care structure and costs.

According to the United Nations 2017 World Population Ageing report, the global population aged 60+ years has more than doubled to 962 million in 2017 compared with 1980 and is expected to double again by 2050 to reach approximately 2.1 billion. Additionally, the number of persons aged 80 years or over will grow even faster than the above rate and is expected to triple between 2017 and 2050 from 137 million to 425 million. By 2030, older persons (aged 60+ years) will outnumber children under the age of 10 and by 2050 will exceed the number of adolescents and youth aged 10-24 years (2.1 billion vs 2 billion). Percentagewise, by 2050, an older population is expected to account for 35 percent of the population in Europe, 28 percent in North America and 25 percent in Latin America.

Today, Japan is the oldest country in the world, with 33.4 percent of population aged 60+ years (4 percent higher than the second oldest country, Italy, with 29.4 percent of 60+ persons). Japan is expected to remain the oldest country in the world until at least 2050 when Japan will have an estimated 42.4 percent of population aged over 60 years.

Population aging in developed countries is a result of two main factors: low fertility rate and increased life expectancy. Thus, in Japan and in some other countries where the overall population is shrinking due to low fertility rates, some of the world's highest life expectancies for both men and women cause rapid increase of the aging population percentage.

In addition to the aging world's population, there is a significant and growing trend, where more and more aged people are living alone. On average, the share of aged people living independently (alone or with spouse only) has increased from 24 percent in 1990 to 37 percent in 2010. The share of independently living aged people is much higher in many developed countries: in the "more developed regions", by the UN classification, the percent of independently living elderly people approaches 75 percent, of which, on the aggregate, 34.5 percent of females and 17 percent of males are living alone.

With the above population aging trends in mind, long-term elderly care (LTC) becomes a problem of national significance in an increasing number of countries. It is estimated that about 70 percent of individuals over age of 65 will require some type of long-term care services during their lifetime. Governments, businesses and non-profit organizations around the world are offering numerous long-term care options. In particular, Long-term care insurance is becoming an organic part of national healthcare insurance systems (available, for example, in the US from private insurers since late 1970's and in Japan municipally since 2000).

Long-term care providers and services in the US include adult day services centers, home health agencies, hospices, nursing homes, and residential care communities. According to a comprehensive 2014 CDC study of long-term care providers, services and users in the US, over six million individuals aged over 65 are receiving help from approximately 63,000 of the above providers and services, including 15600 nursing homes, 30200 residential care communities and excluding 4000 hospices, which provide care to an additional 1.34 million individuals. In Japan, around 25000 specialized long-term care facilities provide long-term elderly care.

One of the most important tasks of the long-term care system for aged individuals is permanent non-invasive monitoring of their condition to ensure their secure stay in long-term care facilities, as well as adequate performance of Activities of Daily Living (ADLs) and prevention of traumas, such as falls (which are known to occur, in particular, for 16 percent of elderly patients at skilled nursing facilities). Video cameras and other invasive tracking methods don't satisfy privacy requirements of elder individuals and may not be used on a permanent basis. Multiple solutions utilizing Wi-Fi networks and compact radars have been recently proposed for the purpose of tracking elderly individuals and other audiences. Examples include the Radar Health Monitor, developed by Kyoto University in partnership with Panasonic and Aura Wi-Fi motion technology by Cognitive Systems Corp.

Notwithstanding noticeable progress in the development of non-invasive tracking technologies and systems for the elderly individuals, the existing solutions are still rudimentary and don't address the majority of issues and tasks at hand. Wi-Fi motion technology uses low-frequency signals and receives negative reviews for its imprecision and failures to detect individual's status. The Radar Health Monitor is focused on monitoring vital signs of individuals, such as a heart rate, which requires static positioning of the individuals; but the existing solution cannot distinguish between a walking, standing and sitting individual and therefore accuracy and even applicability of its measurements at a specific moment may be questionable.

Accordingly, it is desirable to create a technology and system for a comprehensive, non-invasive and intelligent monitoring of elderly individuals.

SUMMARY OF THE INVENTION

According to the system described herein, determining a physical state of a person includes detecting positions of different portions of the person, transforming detected positions of the person into a point cloud having a density that varies according to movement of each of the portions, correlating movement and position data from the point cloud with known physical state positions and transitions between different states, choosing a particular physical state by matching the data from the point cloud with the particular physical state, and obtaining vital signs of the person during an optimal period of time for automatic capturing of vital signs by detecting when the person is in a particular state. The particular state may be a static state. The static state may be standing, sitting, or laying down. The vital signs may include measuring a breathing rate and measuring a heartbeat rate. Vital signs may be obtained by detecting pulsations in the point cloud representing breathing and heartbeats. Positions of different portions of the person may be detected using a non-contact detector. The non-contact detector may be provided by reflections of a radar signal from a wide-band radar. Measured vital signs of the person may be used to detect a dangerous situation for the person. The dangerous situation may be sleep deprivation, sleep apnea, stoppage of breathing, heart disease, arrhythmia, Parkinson's, and/or Alzheimer's. Each of the states may be associated with point densities, sizes, orientations, centers of gravity, and dispositions of bounding boxes of the point clouds. Parametric representations of the bounding boxes, the point densities and positions of the centers of gravity of samples of different states may be provided as input to a neural network classifier. The neural network may be trained by providing the neural network on a server in a cloud computing system that receives data from tracking devices that detect positions of different portions of the person and communicate wirelessly with the cloud computing system. The neural network may be a long short-term memory recurrent neural network. The neural network classifier may correlate movement and position data from the point cloud with known physical state positions and transitions between different states to choose the particular physical state.

According further to the system described herein, a non-transitory computer readable medium contains software that determines a physical state of a person. The software includes executable code that detects positions of different portions of the person, executable code that transforms detected positions of the person into a point cloud having a density that varies according to movement of each of the portions, executable code that correlates movement and position data from the point cloud with known physical state positions and transitions between different states, executable code that chooses a particular physical state by matching the data from the point cloud with the particular physical state, and executable code that obtains vital signs of the person during an optimal period of time for automatic capturing of vital signs by detecting when the person is in a particular state. The particular state may be a static state. The static state may be standing, sitting, or laying down. The vital signs may include measuring a breathing rate and measuring a heartbeat rate. Vital signs may be obtained by detecting pulsations in the point cloud representing breathing and heartbeats. Positions of different portions of the person may be detected using a non-contact detector. The non-contact detector may be provided by reflections of a radar signal from a wide-band radar. Measured vital signs of the person may be used to detect a dangerous situation for the person. The dangerous situation may be sleep deprivation, sleep apnea, stoppage of breathing, heart disease, arrhythmia, Parkinson's, and/or Alzheimer's. Each of the states may be associated with point densities, sizes, orientations, centers of gravity, and dispositions of bounding boxes of the point clouds. Parametric representations of the bounding boxes, the point densities and positions of the centers of gravity of samples of different states may be provided as input to a neural network classifier. The neural network may be trained by providing the neural network on a server in a cloud computing system that receives data from tracking devices that detect positions of different portions of the person and communicate wirelessly with the cloud computing system. The neural network may be a long short-term memory recurrent neural network. The neural network classifier may correlate movement and position data from the point cloud with known physical state positions and transitions between different states to choose the particular physical state.

According further to the system described herein, determining a physical state of a person includes detecting positions of different portions of the person, transforming detected positions of the person into a point cloud having a density that varies according to movement of each of the portions, correlating movement and position data from the point cloud with known physical state positions and transitions between different states, and choosing a particular physical state by matching the data from the point cloud with the particular physical state. Positions of different portions of the person may be detected using a tracking device. The tracking device may be a non-contact tracking device. The tracking device may include at least one wide band radar. The tracking devices may communicate wirelessly with at least one server in a cloud computing system. The states may include walking, standing, sitting, laying down, turning in bed, falling, and/or departed. Falling may be detected in response to the person transitioning from the walking state to the laying down state. During the transitioning, the person may be detected as having a progressively lower center of gravity of the point cloud. An audio generating device may communicate with the person following a fall to confirm the fall and offer basic instructions to the person. A caregiver may be contacted if the person does not move or communicate following the audio generating device communicating with the person. The audio generating device may include a microphone that receives audio communication from the person. Each of the states may be associated with point densities, sizes, orientations, centers of gravity, and dispositions of bounding boxes of the point clouds. Parametric representations of the bounding boxes, the point densities and positions of the centers of gravity of samples of different states may be provided as input to a neural network classifier. The neural network may be trained by providing the neural network on a server in a cloud computing system that receives data from tracking devices that detect positions of different portions of the person and communicate wirelessly with the cloud computing system. The neural network may be a long short-term memory recurrent neural network. The neural network classifier may correlate movement and position data from the point cloud with known physical state positions and may transition between different states to choose the particular physical state. Determining a physical state of a person may also include maintaining information corresponding to customary routine state transitions and locations of the person. Customary routine state transitions and locations may be determined by detecting clusters of points in a multi-dimensional space of sequences of objects, time intervals, locations, and state transitions that represent complex user behaviors. An alarm may be provided to a caretaker in response to the person deviating from the customary routine state transitions and locations. Deviating from the customary routine state transitions and locations may include cycling around a room for a prolonged period of time or repetitively moving back and forth between two objects. The clusters of points corresponding to customary routines may be provided to a cloud computing system for comparison with clusters of points corresponding to customary routines for other people to further categorize behaviors and improve detection of dangerous situations. The person may be in a room and objects in the room may be initially detected by monitoring absolute coordinates of a bounding box of the point cloud in various user states. The objects may include a bed, a table, a chair, a bookshelf, a door, and/or a window. Objects in the room may be detected by subtracting multiple positions of the bounding box from the area of the room. A bed may be detected by observing the person in a laying down state at a certain height off the floor. Boundaries of the bed may be determined by tracking bounding boxes corresponding to a laying down state, a sitting state either before or after entering the laying down state, and a standing state prior to entering the sitting. A bed or a couch may be detected by observing adjacent states of standing, sitting and laying down at a position corresponding to the bed or the couch. A window may be detected by observing the person standing a relatively long time at a boundary of the room.

According further to the system described herein, a non-transitory computer-readable medium contains software that determines a physical state of a person. The software includes executable code that detects positions of different portions of the person, executable code that transforms detected positions of the person into a point cloud having a density that varies according to movement of each of the portions, executable code that correlates movement and position data from the point cloud with known physical state positions and transitions between different states, and executable code that chooses a particular physical state by matching the data from the point cloud with the particular physical state. Positions of different portions of the person may be detected using a tracking device. The tracking device may be a non-contact tracking device. The tracking device may include at least one wide band radar. The tracking devices may communicate wirelessly with at least one server in a cloud computing system. The states may include walking, standing, sitting, laying down, turning in bed, falling, and/or departed. Falling may be detected in response to the person transitioning from the walking state to the laying down state. During the transitioning, the person may be detected as having a progressively lower center of gravity of the point cloud. An audio generating device may communicate with the person following a fall to confirm the fall and offer basic instructions to the person. A caregiver may be contacted if the person does not move or communicate following the audio generating device communicating with the person. The audio generating device may include a microphone that receives audio communication from the person. Each of the states may be associated with point densities, sizes, orientations, centers of gravity, and dispositions of bounding boxes of the point clouds. Parametric representations of the bounding boxes, the point densities and positions of the centers of gravity of samples of different states may be provided as input to a neural network classifier. The neural network may be trained by providing the neural network on a server in a cloud computing system that receives data from tracking devices that detect positions of different portions of the person and communicate wirelessly with the cloud computing system. The neural network may be a long short-term memory recurrent neural network. The neural network classifier may correlate movement and position data from the point cloud with known physical state positions and may transition between different states to choose the particular physical state. The software may also include executable code that maintains information corresponding to customary routine state transitions and locations of the person. Customary routine state transitions and locations may be determined by detecting clusters of points in a multi-dimensional space of sequences of objects, time intervals, locations, and state transitions that represent complex user behaviors. An alarm may be provided to a caretaker in response to the person deviating from the customary routine state transitions and locations. Deviating from the customary routine state transitions and locations may include cycling around a room for a prolonged period of time or repetitively moving back and forth between two objects. The clusters of points corresponding to customary routines may be provided to a cloud computing system for comparison with clusters of points corresponding to customary routines for other people to further categorize behaviors and improve detection of dangerous situations. The person may be in a room and objects in the room may be initially detected by monitoring absolute coordinates of a bounding box of the point cloud in various user states. The objects may include a bed, a table, a chair, a bookshelf, a door, and/or a window. Objects in the room may be detected by subtracting multiple positions of the bounding box from the area of the room. A bed may be detected by observing the person in a laying down state at a certain height off the floor. Boundaries of the bed may be determined by tracking bounding boxes corresponding to a laying down state, a sitting state either before or after entering the laying down state, and a standing state prior to entering the sitting. A bed or a couch may be detected by observing adjacent states of standing, sitting and laying down at a position corresponding to the bed or the couch. A window may be detected by observing the person standing a relatively long time at a boundary of the room.

The proposed system offers a technique, hardware, software and system for permanent tracking of elderly individuals (users) within one or multiple rooms, including detection of a current state of a user, such as walking, standing, sitting, laying down, falling, leaving a room, etc.; capturing and monitoring vital signs of a user, such as breathing and heart rates; detecting objects in a room, such as furniture; identifying customary routes and routines of a user, such as falls or significant deviations from customary routine; using audio recording and automatic voice communications with users to confirm dangerous user states; issuing alerts and warnings to caretakers upon detection and confirmation of dangerous and risk-bearing states. The system is built on compact always-on devices embedded into a room or other facility and including ultra-wideband radars running local software, communicating with cloud-based software and utilizing Artificial Intelligence and Machine Learning to detect user states.

A hardware portion of the system is represented by an always-on tracking device, embedded into a room (for example, plugged into an AC outlet or other power source) and including the following components:

1. One or several ultra-wideband radars, such as frequency-modulated continuous-wave (FMCW) radar(s), with a combined active zone covering the interior of the room.
2. A chipset running firmware and software for local data processing and other operations.
3. A wireless connection with a cellular or other WAN or LAN network for data exchange with a cloud-based portion of the system and over-the-air software and firmware upgrades.
4. An audio recording device.
5. A microphone for communicating with a user and with caretakers.
6. Optionally, a light sensor to measure light intensity and color temperature during user sleep periods.

A tracking device placed in a room is primarily designated for permanent monitoring of a single occupant of the room (user), tracking user's state and performance of ADLs, learning user's habits, adjusting a tracking model (for example, modeling user gait) and customary routines, measuring and gathering statistics on vital signs of a user, determining significant deviations from a regular state, detecting dangerous situations (such as falls or unmotivated wondering around a room), communicating with the user via voice to confirm a dangerous state and offer an immediate advice, and generating warnings or alarms communicated to caretakers. Other tasks include generating user status reports and sharing the user status reports with a user and caretakers. Additional designations of the tracking device may include detecting static or relatively static objects in the room, such as furniture, determining time periods when vital signs of the user can be reliably measured, training the user model, optimizing data exchange and distribution of processing tasks between local and cloud software, upgrading device firmware and software. Additionally, training results and model parameters may be accumulated in the cloud for the purpose of improving models and sharing caretaking experiences.

Tracking devices must not be limited to a single room; for example, several devices may be installed in an adjacent room, a bathroom, etc., jointly monitoring a broader set of user ADLs, routes and routines.

The basic object used in a dynamic modeling of user states is a point cloud, representing body movements of a user and generated by radar(s) of tracking device(s). Density of the cloud and accuracy of the representation may depend on various characteristics of a radar. For a variety of commercially available inexpensive radars, the device may generate on average 50-120 points for a person walking across a room and a geometric approximation of the body may be limited to a dynamically changing bounding box of the point cloud. A user point cloud may reflect substantially two categories of user state: moving (such as walking or moving in a cart across the room, turning in the bed or in a chair, performing exercises such as squats, etc.) and static (standing, sitting, laying down in the bed or on the floor after falling). Density of the user point cloud in a static state may be significantly lower than in a moving state because body movement in a static state is essentially restricted to a chest movement due to breathing and to heartbeats. Point cloud density, along with dimensions and position of the bounding box and the center of gravity of the point cloud, may be used to determine user state by direct geometric processing, by AI methods, such as LSTM (Long short-term memory) based recurrent neural network classifiers, by combined direct/AI methods or otherwise.

Specifically, the system may include the following states for a user and accompanying characteristics of a point cloud, its center of gravity and a bounding box:

W—Walking across the room. The point cloud has a highest density compared with other states, which may depend on the movement direction with respect to the radar wave front. A bounding box has maximum height compared with other states and a center of gravity of the bounding box may vary depending on user gait.

St—Standing in the middle of the room or near an object (chair, table, bookshelf, window, bed, etc.). The point cloud has a low density due to a static position of the user, the bounding box of the captured point cloud is roughly corresponding to the user's chest after an inhale; the center of gravity of the point cloud has the highest vertical position (distance from the floor) among all states.

S—Sitting (on a chair, bed, couch). Dimensions of the bounding box of the point cloud are similar to dimensions during Standing, but the center of gravity of the bounding box is typically lower, i.e. the point cloud is shifted down by a user-specific height interval depending on height of a seat and certain body parameters (leg length, etc.)

L—Laying Down (on a bed couch, etc.). Dimensions of the bounding box are similar to dimensions corresponding to Standing and Sitting, but the bounding box is (i) turned around a horizontal axis by 90 degrees and (ii) raised above the floor level by the height of the bed surface.

T—Turning in the bed. Dimensions and position of the bounding box and the center of gravity are similar to dimensions corresponding to Laying Down. The density of the point cloud is higher than in the Laying Down state due to additional movement.

F—Falling (Laying Down on the floor after falling). Same as Laying Down, except the bounding box is at the floor level.

D—Departed, user is absent from the room. If several devices are installed in a long-term care facility for tracking the user, departing from one room may be accompanied by walking into another room, a bathroom, a patio, etc.

The above list does not exhaust all possible user states. For example, there could be user states specific for bathroom related ADLs, such as taking a shower, taking a bath, shaving, etc.

One important function of the system is periodic measurement and monitoring of vital signs of the user. Vital signs can be reliably captured only in static states (Standing, Sitting, Laying Down); therefore, the proposed system is capable, in contrast with conventional solutions, of detecting optimal periods of time for automatic capturing of vital signs by recognizing user states. The system is also capable of fine-grained differentiation between vital signs taken, for example, in a sitting position vs. during sleep times in a bed. Methods and software for measuring pulsations representing breathing and heartbeats based on reflections of the radar signal are well-known and may be embedded at a firmware level and updated over-the-air when necessary.

Tracking user movements in the Walking state enables modeling user gait based on the periodic change of position of the bounding box and the center of gravity of the point cloud. A unique profile of the user gait, potentially based of a Fourier Transform, can be used, in conjunction with characteristics of the bounding box in other states, for user identification (in case there are several people in the room). The unique profile of the user gait may also be utilized for detecting alarming situations when user gait parameters significantly deviate from normal, for example, limping, uncertain gait, etc.

If a point cloud detected by the tracking device identifies several people in the room, for example, if the cloud is split into two or more disparate clusters of points, indicating the presence of a nurse, a visitor or other people, the system may process the captured information in different ways. In a guest mode, the system may suspend monitoring user states and, accordingly, measuring vital signs (which require determination of a static state, as explained elsewhere herein) until the master user appears alone in the room. A more advanced option may identify the master user based on unique parameters of the point cloud and dynamics of the point cloud (size, gait parameters, etc.) and continue monitoring the master user, ignoring other individuals present in the room.

An oriented State Graph of the system has user states as vertices, whereas edges of the graph are feasible transitions from one state to another. Not all transitions are feasible: for example, a user cannot start walking immediately after laying down on a bed and cannot be standing near a window right after entering the room following a departure.

All possible transitions between user states define elementary user routes, such as entering the room and walking to a chair, standing near a chair, sitting on a chair, walking to the bed, standing near the bed, sitting on the bed, laying down on the bed. Most transitions between states may have specific transition procedures assigned to the transitions; such transition procedures may be verified by the system to improve detection accuracy for user states. For example, in order to transition from the Walking state to the Standing state, a user has to slow down. In another example, when a user is suddenly falling down when walking across the room, the body of the user sharply bends forward or backward; accordingly, bounding boxes of intermediate point clouds captured during the transition from the Walking state to the Falling state progressively decrease heights of the bounding boxes, acquire lower positions of centers of gravity, and increase lengths. Such transitional procedures may be the subject of learning for an LSTM RNN model and the resulting classifiers may employ these procedures to verify the subsequent user states. Alternatively, or additionally to machine learning, transitional procedures may be identified by direct processing of the geometry of point clouds and their bounding boxes.

Elementary user routes may be further combined into customary routines, which may be formally represented as parametrized paths on the State Graph where parameters may include objects in the room, intervals of time spent by a user in each state, etc. An example of a customary routine could be:

D (spending 25 min outside the room)→W (entering the room and walking to the table, 10 sec)→St (standing near a chair, 2 sec)→S (sitting on a chair, 5 min)→W (walking to the window, 15 sec)→St (standing near the window, 2 min)→W (walking to the bed, 7 sec)→St (standing near the bed, 5 sec)→S (sitting on the bed, 90 sec)→L (laying down on the bed, 7 hrs.)

As the installed device monitors user everyday behavior and habits, the system may accumulate a significant number of different customary routines, which may be mapped geometrically as clusters of points in a multi-dimensional space of objects, time intervals and other parameters and may represent complex user behaviors. Subsequently, new routines may be compared with the accumulated clusters and if the new routines stand significantly apart from each of the existing clusters, a signal may be sent to caretakers who may categorize a new routine as a first case of an emerging healthy habit or a deviation from healthy behavior that may require an action on the part of caretakers. The space of customary routines may be transmitted to the cloud and compared with such spaces of other users to further categorize behaviors and improve detection of dangerous situations.

Dangerous situations may be detected by the tracking device using various methods as follows:

Fall detection may be a regular function of state detection engine that may use LSTM classifiers and/or direct geometric processing of point clouds generated by the radar, as explained elsewhere herein (see, for example the description above of a relevant transitional procedure). If a fall is detected, the system may further compare a fragment of an audio record with records for other transitional procedures to confirm the fall. Subsequently, the system may use the microphone of the tracking device to communicate with the user and offer to contact caretakers on behalf of the user or contact caretakers automatically in case the user does not respond.

Erratic or unexplainable behavior, for example, cycling around the room for a prolonged period of time or repetitively moving back and forth between two objects, significantly deviating from customary routines, may be detected using the customary routine detection engine, explained above. Once such behaviors have been detected, the behaviors may be instantly communicated to caretakers via alarm or warning. An attempt to communicate with the user via an audio system of the tracking device may also be an option.

Sleep deprivation may be detected through monitoring vital signs, such as breathing and heart rates and body position of a user laying down for prolonged periods of time. Similar dangerous situation that may be detected include, sleep apnea, stoppage of breathing, heart disease, arrhythmia, Parkinson's, and Alzheimer's.

Undesirable changes in user gait, such as limping, uncertain gait, frequent stops.

Other significant deviations from healthy conditions may rely on monitoring vital signs periodically taken in static user states, as explained above.

At an early state of functioning of a newly installed tracking device, the system may build a portrait of the room, detecting various objects, such as bed, a table, chairs, a bookshelf, a door, a window by monitoring absolute coordinates of a bounding box of a user point cloud in various user states. For example, room areas that are customarily crossed by a walking user, may be subtracted from the space occupied by objects; bounding boxes for adjacent states of standing, sitting and laying down (at a certain height above the floor, corresponding to the height of the bed) may show an approximate position of a bed or a couch. The position and boundaries of a bed or a couch may be further enhanced by monitoring positions of bounding boxes of point clouds for the states of approaching an object prior to the sitting, then sitting down, laying down and reversing these states after waking up. Analogously, a long-time standing near a distant point at a previously detected boundary of the room (using a subtracted walking area) hints at a window.

BRIEF DESCRIPTION OF THE DRAWINGS

Embodiments of the system described herein will now be explained in more detail in accordance with the figures of the drawings, which are briefly described as follows.

FIG. 5 is a schematic illustration of geometry of a falling process, according to an embodiment of the system described herein.

DETAILED DESCRIPTION OF VARIOUS EMBODIMENTS

The system described herein provides a mechanism for continuous, non-invasive and comprehensive monitoring of elderly individuals in long-term care facilities or elsewhere using an ultra-wideband radar-based, internet enabled tracking device and new AI intense geometric methods of processing point cloud for detecting user state, analyzing user behavior, identifying harmful states and conditions, and alerting caretaker when necessary.

Figure 1:
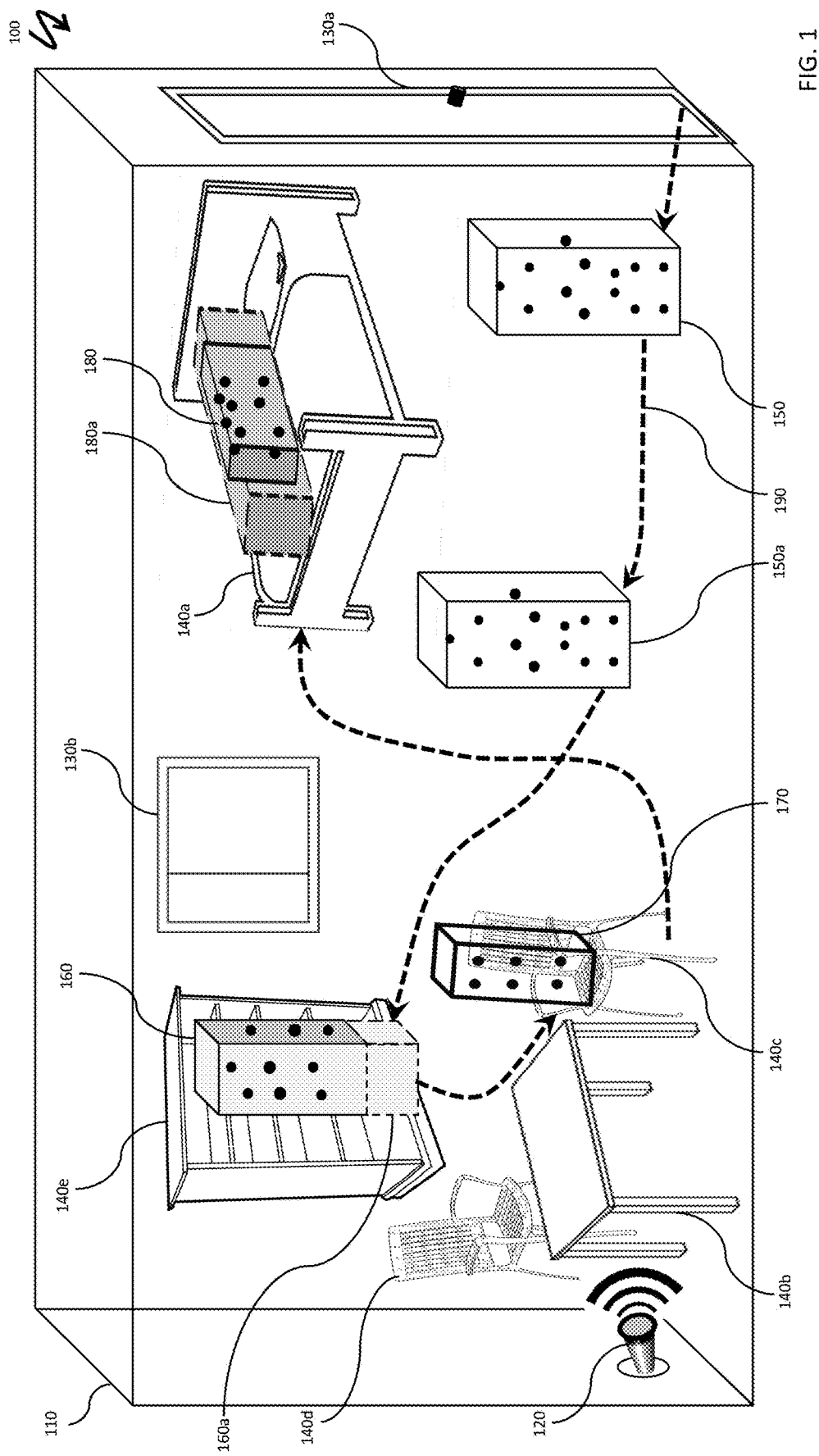
FIG. 1 is a schematic illustration of a room, furniture, tracking device and point clouds for various user states, according to an embodiment of the system described herein.

FIG. 1 is a schematic illustration 100 of a room 110, furniture, tracking device and point clouds for various user states. A long-term care receiver resides in the room 110 that has a tracking device 120 plugged into an AC outlet on a wall. The room 110 has a door 130*a*, a window 130*b* and is furnished with a bed 140*a*, a table 140*b*, a couple of chairs 140*c*, 140*d*, and a bookshelf 140*e*. FIG. 1 illustrates one dynamic user state—Walking 150, 150*a*, with denser point clouds and larger size of bounding boxes, and three static user states:

Standing near the bookshelf 140*e*—a larger box 160*a* shows a larger portion of the body of the user, which does not generate radar points due to static position, while the chest portion 160 generates points due to user breathing.

Sitting on the chair 140*c*—only the chest portion 170 and the actual point cloud and the bounding box of the chest portion 170 are shown.

Laying Down on the bed 140*a*—similar to the case of Standing, only the chest portion 180 generates points within the body 180*a*.

Figure 2:
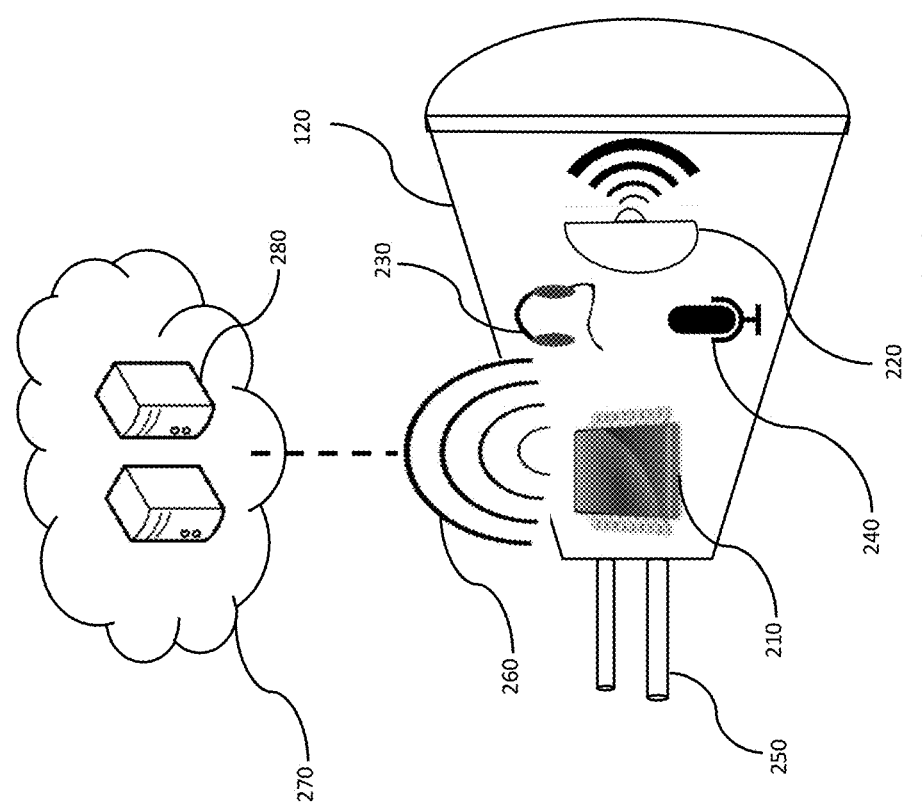
FIG. 2 is a schematic illustration of a tracking device, according to an embodiment of the system described herein.

FIG. 2 is a schematic illustration 200 of a tracking device 120. A chipset 210 enables data collection, processing and data exchange with the cloud. An ultra-wideband radar 220 has a coverage area close to 180 degrees and tracks moving objects in the room. In case less expensive radars with a smaller capturing angle are utilized, the tracking device 120 may include a couple of such less advanced radars with their corresponding capturing areas turned with respect to each other around a vertical axis to provide a broader combined capturing area. An audio recording device 230 is used to capture sounds of activities of daily living and user routines and potentially compare the activities of daily living and user routines with unusual sound tracks recorded during alarming activities. A microphone or other audio generating device 240 may be used to communicate with a user (for example, to confirm a fall and offer basic instructions) or with caretakers. A power plug 250 is self-explanatory. A cellular, Wi-Fi or other internet connection 260 may be used to exchange data between the tracking device 120 and the cloud 270 where portion of the system software may be running on servers 280.

Figure 3:
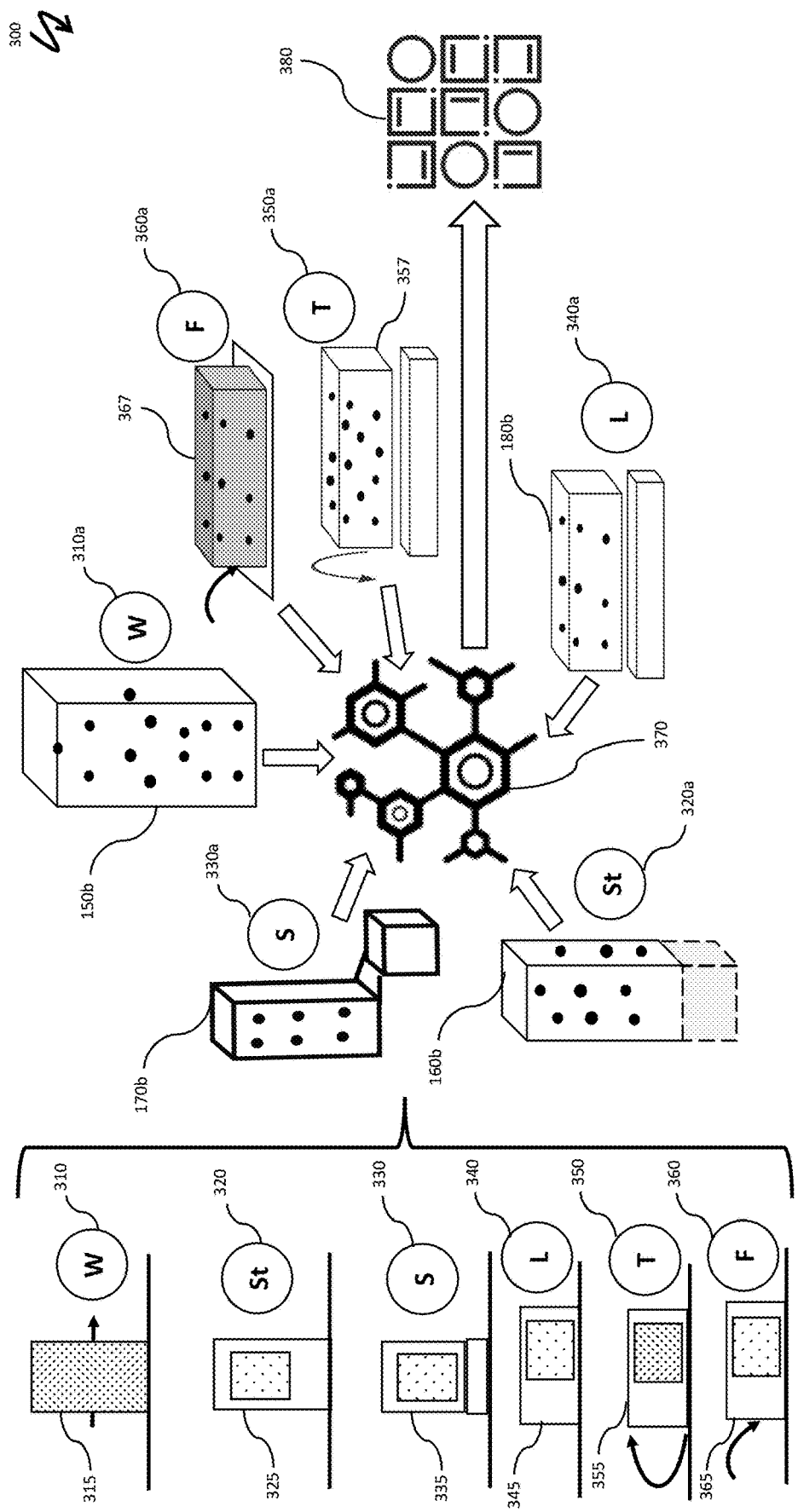
FIG. 3 is a schematic illustration of user states and a neural network based classifier, according to an embodiment of the system described herein.

FIG. 3 is a schematic illustration 300 of user states and a neural network based classifier. User states are explained elsewhere herein: Walking—310, Standing—320, Sitting—330, Laying Down (on a bed, couch, etc.)—340, Turning in bed—350, Falling—360 are associated with characteristic point densities, sizes, orientations and dispositions of bounding boxes of point clouds, mnemonically shown by items 315, 325, 335, 345, 355, 365. Parametric representations of characteristic bounding boxes, point densities and positions of gravity centers constitute learning material for a neural network classifier. Accordingly, data from real life and early, radar captured samples of point clouds, normalized within the bounding boxes 150*b*, 160*b*, 170*b*, 180*b*, 357, 367, similar to illustrations of bounding boxes of point clouds in FIG. 1, associated with relevant user states 310*a*, 320*a*, 330*a*, 340*a*, 350*a*, 360*a* are fed into a machine learning subsystem 370, such as an LSTM model for recurrent neural networks. A resulting classifier 380 may become a principal system component for subsequent continuous identification of user states.

Figure 4:
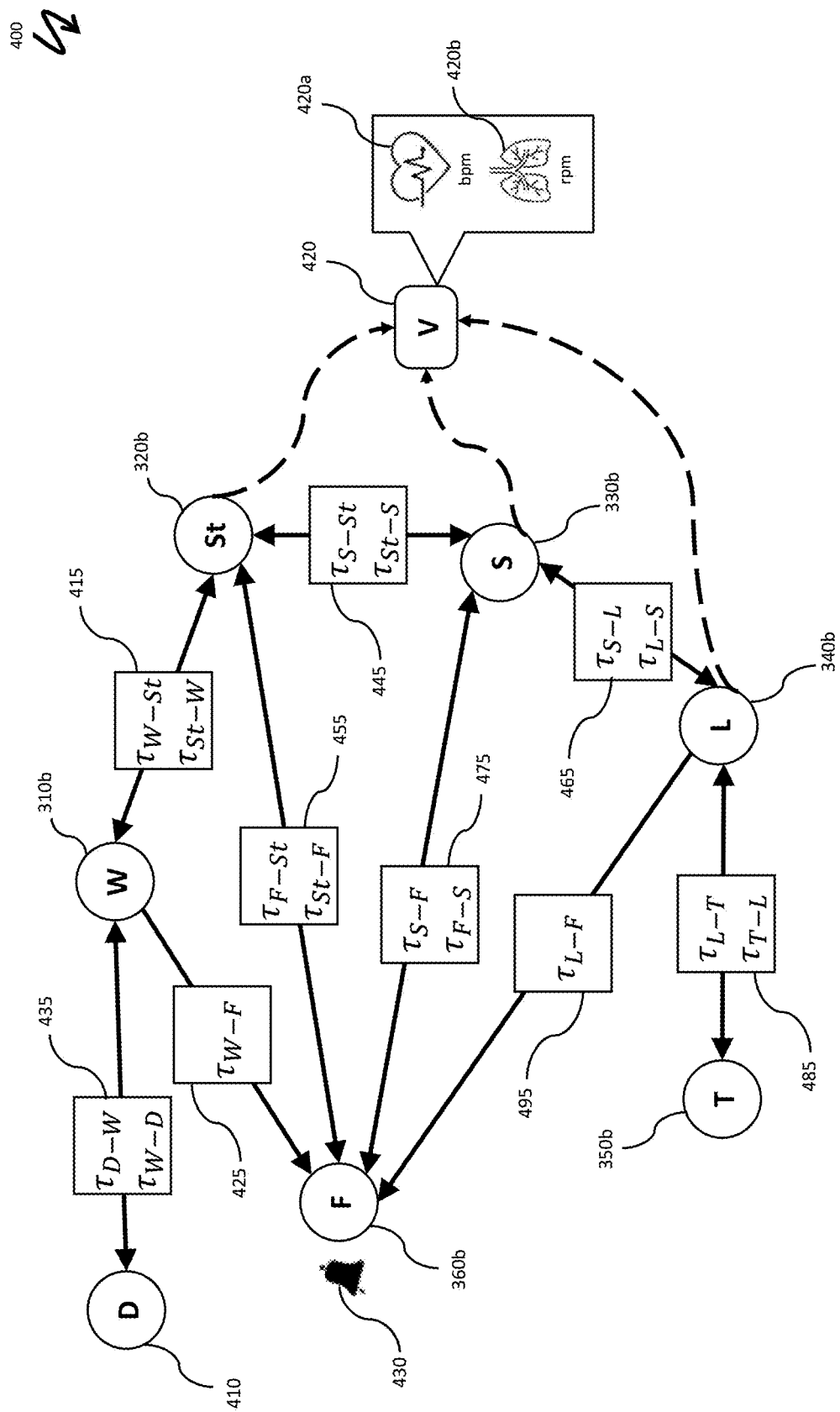
FIG. 4 is a schematic illustration of a user state graph, according to an embodiment of the system described herein.

FIG. 4 is a schematic illustration 400 of a user state graph. Various user states 310*b*, 320*b*, 330*b*, 340*b*, 350*b*, 360*b*, 410 represent vertices of the state graph. Oriented edges of the graph are represented by bold arrows and show possible transitions between states. For some user states, transitions may occur in both directions, for example, the Walking state 310*b* may be followed by the Standing state 320*b*, and vice versa. At the same time, the Walking state 310*b* may be followed by the Falling state 360*b*, but reverse transition is not possible (at the very least, a user has to stand up and then walk, which corresponds to edges in both directions between the Falling state 360*b* and the Standing state 320*b*).

Each feasible transition between user states is associated with a transition procedure. There are a total of sixteen transition procedures, such as slowing down when the Walking state 310*b* transitions to the Standing state 320*b* or bending forward or backward when the Walking state 310*b* transitions to the Falling state 360*b*: 14 of the transition procedures are associated with seven pairs of vertices where transitions are available in both directions, namely, transition modules 415, 435, 445, 455, 465, 475, 485 include two transitions each, whereas two transitions 425, 495 are available only in one direction.

Machine learning may include learning characteristics and parameters of bounding boxes of point clouds captured for transition procedures and recognizing new states by checking transitional procedures leading to the new states. Alternatively, transitional procedures may be verified via direct geometric computations using, for example, back-tracking of recorded user trajectories leading to a certain condition.

Two of the user states 310*b*, 350*b* in FIG. 4 are dynamic, three states 320*b*, 330*b*, 340*b* are static, one state 410 shows absence of the user, one state 360*b* is dangerous and may be accompanied by an alert or warning 430, as explained elsewhere herein. Dashed arrows connecting static states with a vital signs measurement module 420 illustrate optimization of capturing of vital signs, such as heart rate 420*a* and breathing rate 420*b* (as explained elsewhere herein).

FIG. 5 is a schematic illustration 500 of geometry of a falling process. In a basic geometric model discussed herein where user position is represented by a bounding box of a point cloud captured by tracking device's radar(s) the system recognizes bounding boxes parallel to three-dimensional coordinate axes. Therefore, when a user starts with a walking state 150c and bends, for example, forward, intermediate positions of the user body may be illustrated by slanted boxes 510, 530; however, the system only recognizes canonical bounding boxes and replaces the slanted boxes 510, 530 with standard bounding boxes 520, 540, having progressively lower positions of centers of gravity and vertical heights and transitioning to a final state 367a. The geometric characteristics may be captured directly by the user trajectory processing software or may be taken into account by automatic classifiers, as explained in conjunction with FIG. 4.

Figure 6:
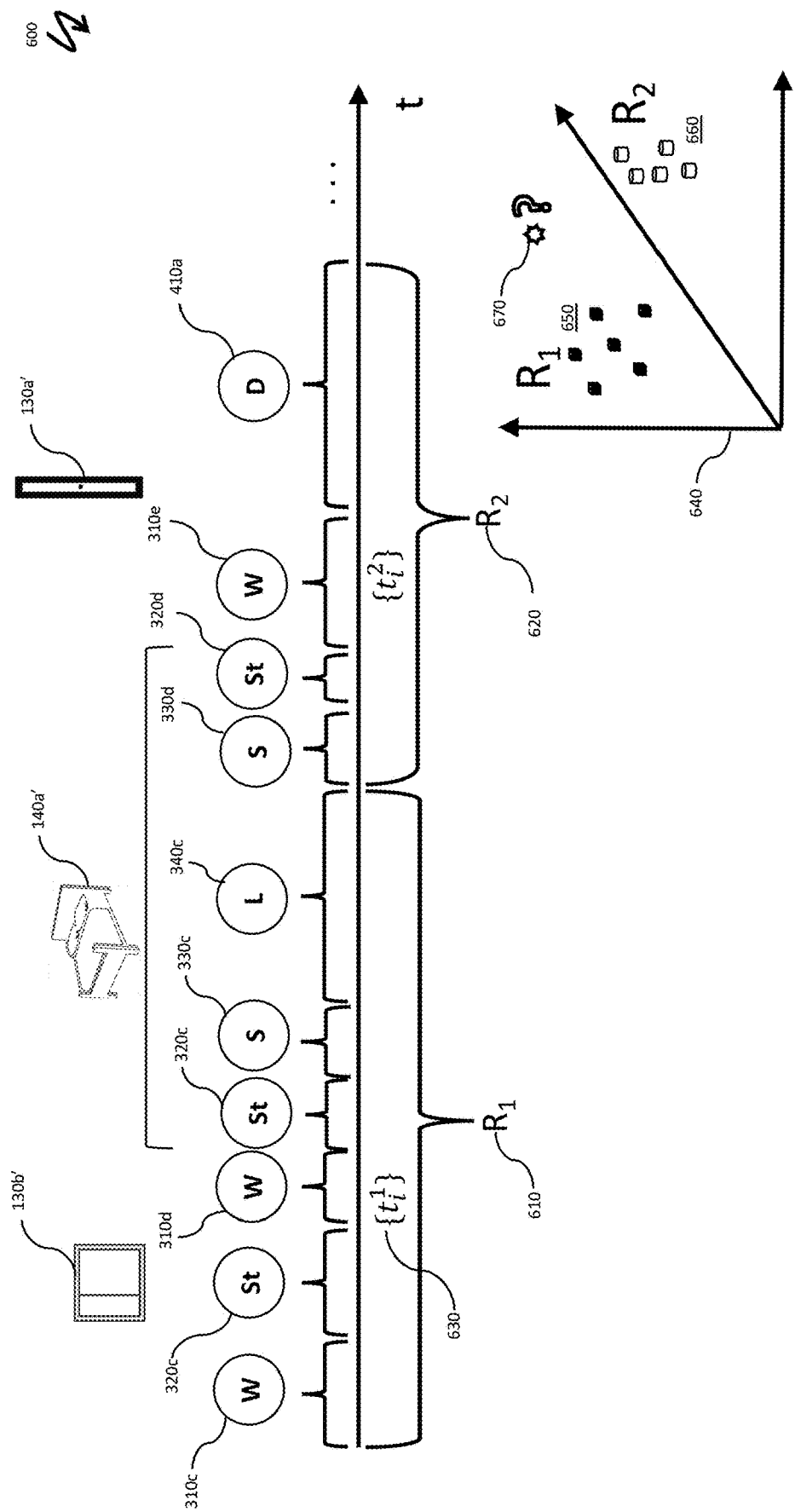
FIG. 6 is a schematic illustration of customary routines and related clusters, according to an embodiment of the system described herein.

FIG. 6 is a schematic illustration 600 of customary routines and related clusters in a multi-dimensional space of objects and time intervals. A continuous long-time monitoring of everyday user behavior and habits may reveal a set of customary routines followed by a user. A routine may be defined as a frequently repeated sequence of states, related objects, time intervals for staying in each state and other associated parameters. In FIG. 6, two examples of customary routines are illustrated:

A first routine 610 ($R_1$) includes six user states—Walking 310c, Standing 320c near the window 130b', Walking 310d from the window to the bed 140a', Standing 320c near the bed and Sitting 330c on the bed for short periods of time and Laying Down 340c on the bed for a prolonged period of time. A second routine 620 ($R_2$) starts at the end of the first routine and include four user states—Sitting 330d on the bed 140a' (after laying down for a long time), Standing up 320d, Walking 310e out of the room through the door 130a' and staying out of the room (Departed state 410a) for a prolonged period of time.

Both sequences of user states forming the routines 610, 620 may repeat many times daily; time intervals 630 for staying in each state will, obviously, vary; objects encountered by the user along each routine may also vary. Thus, while the bed may remain the final point of the first routine (and the starting point of the second routine), the window 130b' may be replaced, for example, by the bookshelf 140e (see FIG. 1). Different instances of a customary routine may be construed as points in a multidimensional space 640, where coordinates may represent, for example, objects in the room and time sequences reflecting stay times for each state in a routine. Clusters of points 650, 660 represent customary routines. Accordingly, a new routine detected by the system may be analogously denoted as a point 670 in the same space; if the point is located far away from existing clusters, the point may be automatically marked as a new routine or an alarming sequence of states that has to be explained by caretakers or the user.

Figure 7:
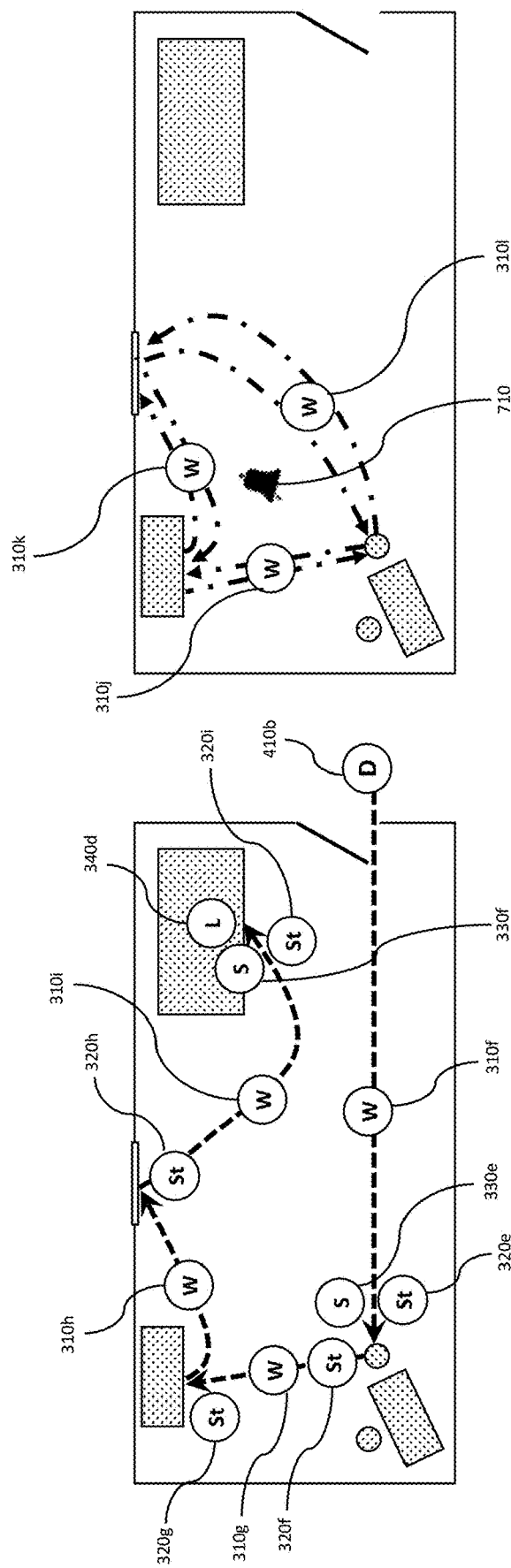
FIGS. 7A-7B are schematic illustrations of ordinary and alarming user routines, according to an embodiment of the system described herein.

FIGS. 7A-7B are schematic illustrations of ordinary and alarming user routines captured by the system.

FIG. 7A illustrates an ordinary routine, potentially combining two independent customary routines, one of which has been explained in conjunction with FIG. 6. The routine includes entering the room, walking to a chair, standing and sitting down on the chair (a state 410b to a state 310f to states 320e to a state 330e); then standing up, walking to the bookshelf and standing near the bookshelf (a state 320f to a state 310g to a state 320g); walking to the window and standing near the window, then walking to the bed, standing, sitting and laying down (a state 310h to a state 320h to a state 310i to a state 320i to a state 330f to a state 340d, which coincides with the customary routine 620 in FIG. 6). With reasonable time intervals occupied by each user state in the routine, it is quite ordinary and does not cause the system to suspect any alarming situation.

FIG. 7B illustrates a different example of a user routine. Here, a user is walking between a chair, the bookshelf and the window altering states 310j, 310k, 310l, without stopping or sitting and randomly changing walking directions (as shown by directions of dash-dotted arrows). Such restless behavior may show discomfort or anxiety of the user and may cause the system to generate an alert 710 and notify caretakers. The system may also attempt communicating with the user via the audio system (microphone) to clarify user behavior.

Figure 8:
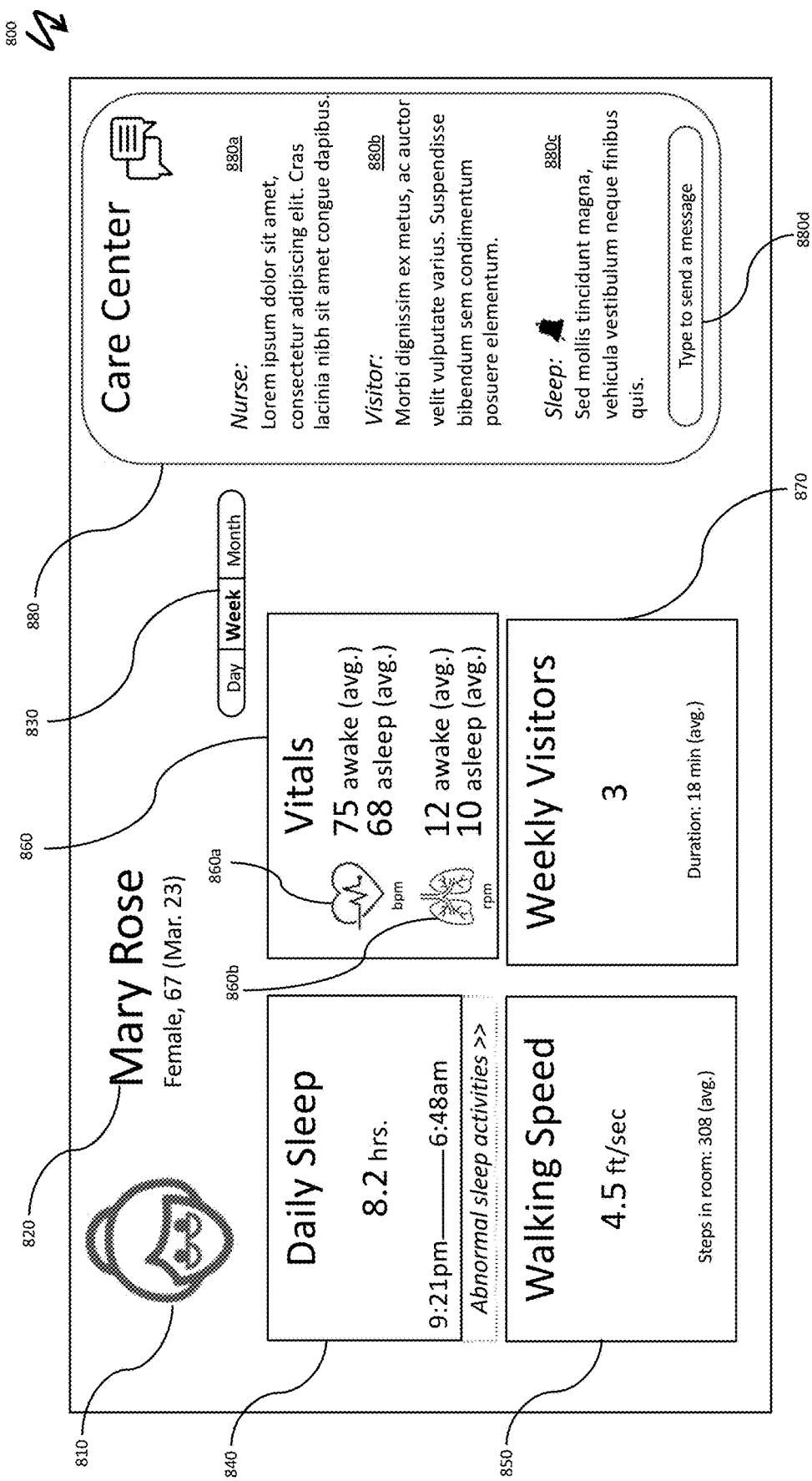
FIG. 8 is a schematic illustration of a system dashboard, according to an embodiment of the system described herein.

FIG. 8 is a schematic illustration 800 of a system dashboard that may be displayed to caretakers and possibly to a user 810. The dashboard may include personal data 820 of the user 810, timeframe choices 830 for calculating user statistics, daily sleep averages 840 for a chosen timeframe, average walking statistics 850, vital signs statistics 860, such as heart rate 860a and breathing rate 860b measured in awake and sleeping conditions, average number and duration of stay of visitors 870. Such an electronic dashboard may also include an interactive panel 880 for communications with a care center. Example of messages may include communications between nurses and visitors 880a, 880b entered via message field 880d, current user state statistics and alerts 880c (entered automatically), etc.

Figure 9:
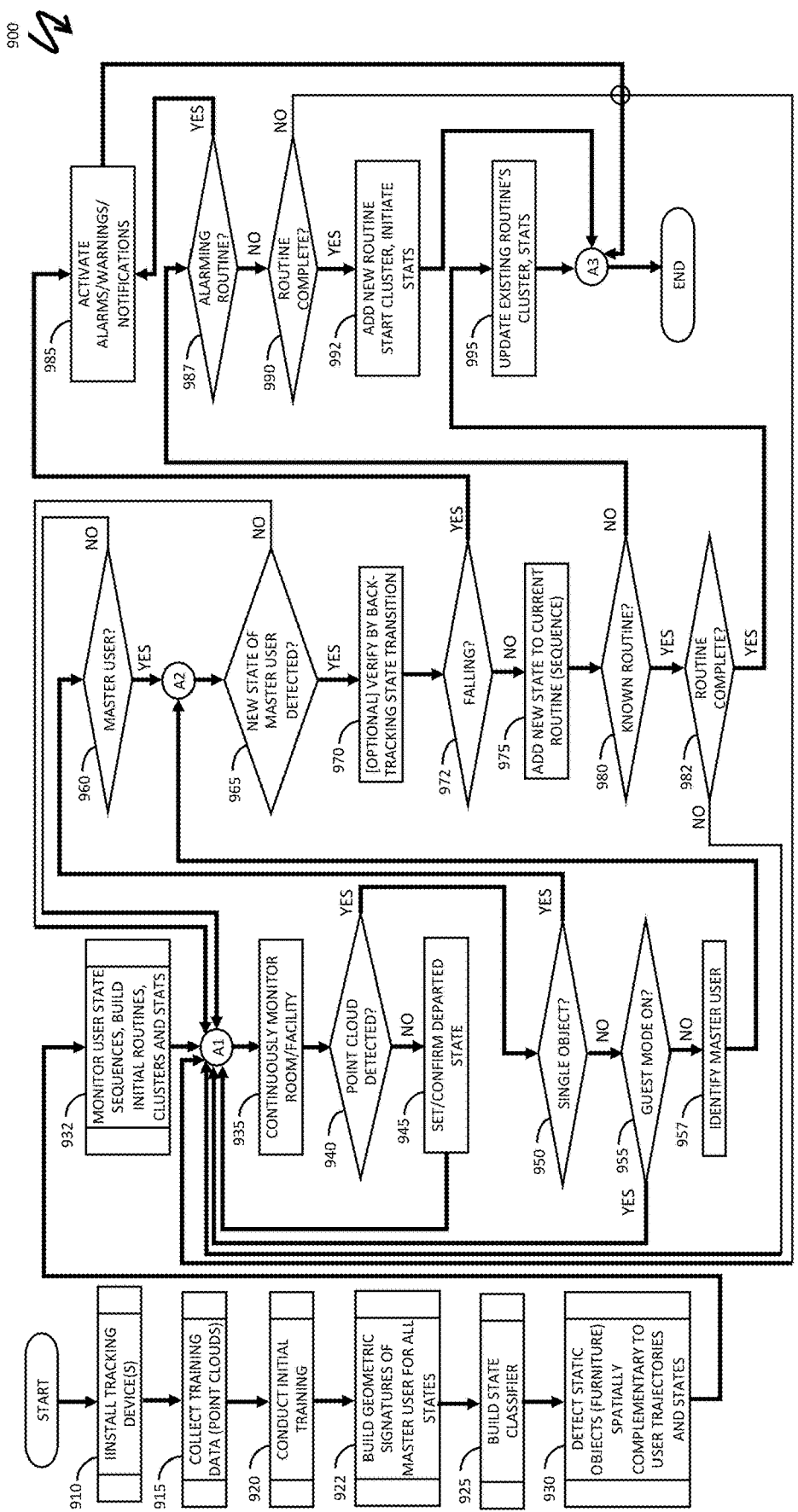
FIG. 9 is a system flow diagram illustrating system functioning in connection with identifying and categorizing user states and routines, according to an embodiment of the system described herein.

Referring to FIG. 9, a system flow diagram 900 illustrates system functioning in connection with identifying and categorizing user states and routines. Processing begins at a step 910, where one or more tracking devices are installed on long-term care premises, such as a user room. After the step 910, processing proceeds to a step 915, where training data in the form of point clouds captured by the radar(s) included with tracking device(s) are collected. After the step 915, processing proceeds to a step 920, where an initial round of training is conducted, as explained elsewhere herein (see, for example, FIG. 3 and the accompanying text). After the step 920, processing proceeds to a step 922, where a geometric signature of a master user is built for all user states for the purpose of user identification in situations when there are multiple users in the room or when a master user may be temporarily absent from the room. After the step 922, processing proceeds to a step 925, where a state classifier is initially built, as explained, for example, in FIG. 3 and the accompanying text. After the step 925, processing proceeds to a step 930, where the system detects static objects in the room, such as furniture, based on a complementary location of the furniture with respect to user trajectories and user states. After the step 930, processing proceeds to a step 932, where the system monitors sequences of detected user states, builds initial routines, routine clusters and stats (see, in particular, FIG. 6 and the accompanying text).

After the step 932, processing proceeds to a step 935, where the system and the tracking device(s) continuously monitor the room or other facility. After the step 935, processing proceeds to a test step 940, where it is determined whether a point cloud is detected by the tracking device. If not, processing proceeds to a step 945, where the Departed user state is set or confirmed by the system (see FIGS. 3, 4, 6, 7 and the accompanying texts for further explanations). After the step 945, processing proceeds back to the monitoring step 935, which may be independently reached from the step 932. If it is determined at the test step 940 that a point cloud was detected, processing proceeds to a test step 950, where it is determined whether the point cloud corresponds to a single object. If not, processing proceeds to a test step 955, where it is determined whether a guest mode of the system is on (in the guest mode, the tracking device suspends tracking details of the master user until the master user is found alone in the room). If so, processing proceeds back to the monitoring step 935, which may be independently reached from the steps 932 and 945. Otherwise, processing proceeds to a step 957, where the system identifies the master user's point cloud, as explained elsewhere herein.

After the step 957, processing proceeds to a test step 965 explained below. If it was determined at the text step 950 that the point cloud corresponds to a single object, processing proceeds to a test step 960, where it is determined whether the detected object is the master user. If so, processing proceeds to the test step 965, which may be independently reached from the step 957; otherwise, processing proceeds back to the monitoring step 935, which may be independently reached from the steps 932, 945 and the test step 955 (the system monitors only the master user and ignores other individuals that may appear alone in the room, for example, a caretaker or a service person who entered the room when the master user left the room for a breakfast). At the test step 965, it is determined whether a new state of the master user has been detected. If not, processing proceeds back to the monitoring step 935, which may be independently reached from the steps 932, 945 and the test steps 955, 960. Otherwise, processing proceeds to a step 970, where the system may optionally verify the new state by geometric back-tracking of the transition phase to the new user state from the previous user state, as explained elsewhere herein (see, in particular, FIG. 4 and the accompanying text).

After the step 970, processing proceeds to a test step 972, where it is determined whether the new user state is Falling. If so, processing proceeds to a step 985, where the system generates and activates alarms, warnings and notifications (including potential audio communications with the user, as explained elsewhere herein). After the step 985, processing is complete. If it was determined at the test step 972 that the current user state is not Falling, processing proceeds to a step 975, where the new user state is added to the current user routine (sequence of user states, explained, for example, in FIGS. 6,7 and the accompanying texts). After the step 975, processing proceeds to a test step 980, where it is determined whether the current routine is known to the system (recorded previously as a complete or partial routine). If so, processing proceeds to a test step 982, where it is determined whether the current routine is complete (for example, has been recorded previously as a customary routine, as explained elsewhere herein). If not, processing proceeds back to the monitoring step 935, which may be independently reached from the steps 932, 945 and the test steps 955, 960, 965. Otherwise, processing proceeds to a step 995, where the statistics and the cluster representation of the current routine in the multidimensional space (see FIG. 6 and the accompanying text for details) are updated. After the step 995, processing is complete.

If it has been determined at the test step 980 that the current routine is unknown (was never recorded previously), processing proceeds to a test step 987, where it is determined whether the current routine appears alarming, as explained, for example, in conjunction with FIG. 7B. If so, processing proceeds to the step 985, which may be independently reached from the test step 972. Otherwise, processing proceeds to a test step 990, where it is determined whether the (new, unknown previously) routine appears complete (or may be declared complete according to the system criteria). If not, processing proceeds back to the monitoring step 935, which may be independently reached from the steps 932, 945 and the test steps 955, 960, 965, 982. Otherwise, processing proceeds to a step 992, where a new routine is added to the system and the associated cluster in the multidimensional space and the statistics are initiated. After the step 992, processing is complete.

Various embodiments discussed herein may be combined with each other in appropriate combinations in connection with the system described herein. Additionally, in some instances, the order of steps in the flowcharts, flow diagrams and/or described flow processing may be modified, where appropriate. Subsequently, system configurations and functions may vary from the illustrations presented herein. Further, various aspects of the system described herein may be implemented using various applications and may be deployed on various devices, including, but not limited to smartphones, tablets and other mobile computers. Smartphones and tablets may use operating system(s) selected from the group consisting of: iOS, Android OS, Windows Phone OS, Blackberry OS and mobile versions of Linux OS. Mobile computers and tablets may use operating system selected from the group consisting of Mac OS, Windows OS, Linux OS, Chrome OS.

Software implementations of the system described herein may include executable code that is stored in a computer readable medium and executed by one or more processors. The computer readable medium may be non-transitory and include a computer hard drive, ROM, RAM, flash memory, portable computer storage media such as a CD-ROM, a DVD-ROM, a flash drive, an SD card and/or other drive with, for example, a universal serial bus (USB) interface, and/or any other appropriate tangible or non-transitory computer readable medium or computer memory on which executable code may be stored and executed by a processor. The software may be bundled (pre-loaded), installed from an app store or downloaded from a location of a network operator. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of determining a physical state of a person, comprising:
    detecting positions of different portions of the person;
    transforming detected positions of the person into a point cloud having a density that varies according to movement of each of the portions;
    correlating movement and position data from the point cloud with known physical state positions and transitions between different states;
    choosing a particular physical state by matching the data from the point cloud with the particular physical state; and
    obtaining vital signs of the person during an optimal period of time for automatic capturing of vital signs by detecting when the person is in a particular state.

2. A method, according to claim 1, wherein the particular state is a static state.

3. A method, according to claim 2, wherein the static state is one of: standing, sitting, or laying down.

4. A method, according to claim 1, wherein the vital signs include measuring a breathing rate and measuring a heartbeat rate.

5. A method, according to claim 4, wherein vital signs are obtained by detecting pulsations in the point cloud representing breathing and heartbeats.

6. A method, according to claim 5, wherein positions of different portions of the person are detected using a non-contact detector.

7. A method, according to claim 6, wherein the non-contact detector is provided by reflections of a radar signal from a wide-band radar.

8. A method, according to claim 1, wherein measured vital signs of the person are used to detect a dangerous situation for the person.

9. A method, according to claim 8, wherein the dangerous situation is one or more of: sleep deprivation, sleep apnea, stoppage of breathing, heart disease, arrhythmia, Parkinson's, or Alzheimer's.

10. A method, according to claim 1, wherein each of the states is associated with point densities, sizes, orientations, centers of gravity, and dispositions of bounding boxes of the point clouds.

11. A method, according to claim 10, wherein parametric representations of the bounding boxes, the point densities and positions of the centers of gravity of samples of different states are provided as input to a neural network classifier.

12. A method, according to claim 11, wherein the neural network is trained by providing the neural network on a server in a cloud computing system that receives data from tracking devices that detect positions of different portions of the person and communicate wirelessly with the cloud computing system.

13. A method, according to claim 12, wherein the neural network is a long short-term memory recurrent neural network.

14. A method, according to claim 11, wherein the neural network classifier correlates movement and position data from the point cloud with known physical state positions and transitions between different states to choose the particular physical state.

15. A non-transitory computer readable medium containing software that determines a physical state of a person, the software comprising:

executable code that detects positions of different portions of the person;

executable code that transforms detected positions of the person into a point cloud having a density that varies according to movement of each of the portions;

executable code that correlates movement and position data from the point cloud with known physical state positions and transitions between different states;

executable code that chooses a particular physical state by matching the data from the point cloud with the particular physical state; and executable code that obtains vital signs of the person during an optimal period of time for automatic capturing of vital signs by detecting when the person is in a particular state.

16. A non-transitory computer readable medium, according to claim 15, wherein the particular state is a static state.

17. A non-transitory computer readable medium, according to claim 16, wherein the static state is one of: standing, sitting, or laying down.

18. A non-transitory computer readable medium, according to claim 15, wherein the vital signs include measuring a breathing rate and measuring a heartbeat rate.

19. A non-transitory computer readable medium, according to claim 18, wherein vital signs are obtained by detecting pulsations in the point cloud representing breathing and heartbeats.

20. A non-transitory computer readable medium, according to claim 19, wherein positions of different portions of the person are detected using a non-contact detector.

21. A non-transitory computer readable medium, according to claim 20, wherein the non-contact detector is provided by reflections of a radar signal from a wide-band radar.

22. A non-transitory computer readable medium, according to claim 15, wherein measured vital signs of the person are used to detect a dangerous situation for the person.

23. A non-transitory computer readable medium, according to claim 22, wherein the dangerous situation is one or more of: sleep deprivation, sleep apnea, stoppage of breathing, heart disease, arrhythmia, Parkinson's, or Alzheimer's.

* * * * *